United States Patent [19]

Hirai et al.

[11] Patent Number: 5,198,013
[45] Date of Patent: Mar. 30, 1993

[54] BENZOXAZINONE COMPOUNDS AND HERBICIDAL COMPOSITION CONTAINING THE SAME

[75] Inventors: Kenji Hirai, Kanagawa; Atsuko Fujita, Chiba; Hiroshi Sato, Chiba; Hiroaki Hirose, Chiba; Masahiro Yokota, Chiba; Shoin Nagato, Tokyo, all of Japan

[73] Assignees: Sagami Chemical Research Center, Tokyo; Chisso Corporation, Osaka; Kaken Pharmaceutical Co., Ltd., Tokyo, all of Japan

[21] Appl. No.: 301,419

[22] Filed: Jan. 25, 1989

[30] Foreign Application Priority Data

| Feb. 5, 1988 | [JP] | Japan | 63-25492 |
| Feb. 5, 1988 | [JP] | Japan | 63-25493 |
| Jan. 17, 1989 | [JP] | Japan | 1-7942 |
| Jan. 17, 1989 | [JP] | Japan | 1-7943 |

[51] Int. Cl.⁵ .................. A01N 43/84; C07D 413/04
[52] U.S. Cl. ..................................... 504/225; 544/105
[58] Field of Search ................... 544/105; 71/88

[56] References Cited

U.S. PATENT DOCUMENTS

3,966,750  6/1976  Mangold et al. ............... 260/307
4,818,272  4/1989  Hirai et al. ....................... 71/88

FOREIGN PATENT DOCUMENTS

0241559 10/1987 European Pat. Off. .
3607068  9/1987 Fed. Rep. of Germany .
0044587  4/1978 Japan .
170191A  2/1986 Japan .
176101A  4/1986 Japan .
273822  9/1977 U.S.S.R. .
1297346 11/1972 United Kingdom .

OTHER PUBLICATIONS

CA 108:89485f, 1988, Pissiotas et al., "Preparation of N-Phenyl-3,4,5,6-tetrahydrophthaimide derivatives and their use as herbicides".
Patent Abstracts of Japan 10, No. 245, (C–368) (2301).
Patent Abstracts of Japan 10, No. 182, (C–359) (2238).
Patent Abstracts of Japan 11, No. 246, (C–439) (2693).

*Primary Examiner*—Alan L. Rotman
*Assistant Examiner*—Celia Chang
*Attorney, Agent, or Firm*—Nixon & Vanderhye

[57] ABSTRACT

A benzoxazinone compound represented by the formula (I):

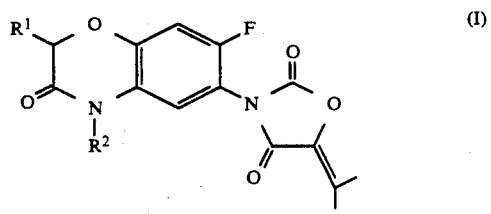

wherein $R^1$ represents a hydrogen atom or an alkyl group, and $R^2$ represents a hydrogen atom, an alkyl group, a cyanoalkyl group, an alkenyl group, an alkynyl group or an aralkyl group; a process for preparing the same; and a herbicidal composition comprising the benzoxazinone compound as an active component are disclosed. The above benzoxazinone compounds exhibit a high selectivity for useful crop plants and a strong herbicidal activity with respect to various noxious weeds.

9 Claims, No Drawings

BENZOXAZINONE COMPOUNDS AND HERBICIDAL COMPOSITION CONTAINING THE SAME

FIELD OF THE INVENTION

This invention relates to novel benzoxazinone compounds, a process for preparing the benzoxazinone compounds, and a herbicidal composition containing the benzoxazinone compound as an active component.

BACKGROUND OF THE INVENTION

The benzoxazinone compounds according to the present invention are represented by the formula (I):

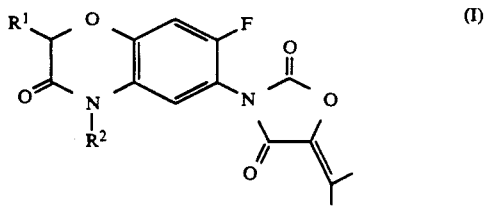

wherein $R^1$ represents a hydrogen atom or an alkyl group, and $R^2$ represents a hydrogen atom, an alkyl group, a cyanoalkyl group, an alkenyl group, an alkynyl group or an aralkyl group.

Hitherto, various types of oxazolidinedione compounds having a substituent at the 5-position of the oxazolidinedione ring have been known, but oxazolidinedione compounds having a substituted methylidene group at the 5-position have not been reported in view of the fact that the synthesis of these compounds has been considered very difficult. Further, although various types of heterocyclic compounds having a herbicidal activity have been reported in various publications and have been practically used to date, no oxazolidinedione type compounds have been known to have a practically useful herbicidal activity.

Of the conventionally known oxazolidinedione compounds, compounds having a substituted or unsubstituted phenyl group on the nitrogen atom at the 3-position and having an alkylidene group at the 5-position have been reported to have a herbicidal activity against various weeds as described in Japanese Patent Application (Kokai) No. 62-174065 (the term "Kokai" as used herein means an unexamined published application), but this prior art reference does not teach or suggest the physiological activity of compounds having a bicyclic substituted phenyl group such as a compound having a benzoxazinone ring.

As a result of extensive studies on various oxazolidinedione derivatives, the present inventors found that these novel oxazolidinedione compounds having an isopropylidene group at the 5-position and having a substituted benzoxazine on the nitrogen atom at the 3-position, i.e., the benzoxazinone compounds represented by the formula (I) above, exhibit a strong herbicidal activity against various weeds at a relatively low dose and can be practically used as a herbicidal agent. On this basis they completed the present invention.

SUMMARY OF THE INVENTION

An object of the present invention is therefore to provide novel benzoxazinone compounds represented by the formula (I) above having both a high selectivity for useful crop plants and a high herbicidal activity against various strongly noxious weeds.

Another object of the present invention is to provide a process for preparing these benzoxazinone compounds.

A further object of the present invention is to provide a herbicidal composition comprising a benzoxazinone compound as an active component.

DETAILED DESCRIPTION OF THE INVENTION

The benzoxazinone compounds according to the present invention exhibit a strong herbicidal activity against annual weeds such as *Echinochloa crus-galli, Monochoria vaginalis, Ammannia multiflora*, etc., as well as pernnial weeds such as *Cyperus serotinus, Scirpus juncoides, Sagittaria pygmaea, Eleocharis acicularis*, etc., when used in the paddy field, and also exhibit a selective withering activity on field weeds such as *Amaranthus lividus, Digitaria adscendens, Setaria viridis, Chenopodium album, Polygonum longisetum, Amaranthus viridis, Portulaca oleracea, Plantago asiatica*, etc.

Further, since the benzoxazinone compounds of the present invention possess a strong herbicidal activity, these compounds exhibit the desired herbicidal effect at a relatively low dose and also have a relatively small phytotoxicity to useful crop plants. That is, the benzoxazinone compounds according to the present invention exhibit a withering effect on graminaceous weeds such as *Echinochloa crus-galli, Digitaria sanguinalis, Setaria viridis*, etc., but these compounds show substantially no phytotoxicity to graminaceous crops such as transplanted paddy rice, wheat, corn, etc. In addition, these compounds show substantially no phytotoxicity to crops other than graminaceous crops such as soybean, cotton, etc.

The herbicidal composition containing at least one of the benzoxazinone compounds represented by the formula (I) as an active component can be used in various amounts depending upon the type of method employed for application, the time of application, and the kind of plant species to which the herbicidal composition is applied, but generally the compound can be applied in an amount of from about 10 to about 500 g, preferably 30 to 300 g, per Are, preferably in the form of an emulsion, wettable power, dust preparation or granule preparation, as described hereinafter in detail.

The novel benzoxazinone compounds represented by the formula (I) above according to the present invention can be prepared by Process 1 or 2 described below.

Process 1

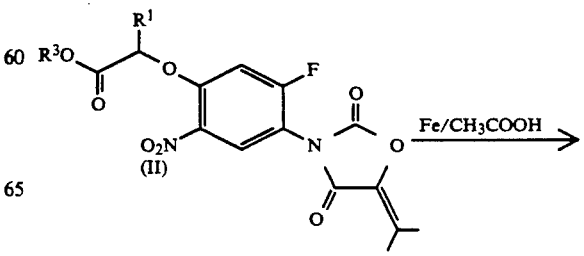

-continued
Process 1

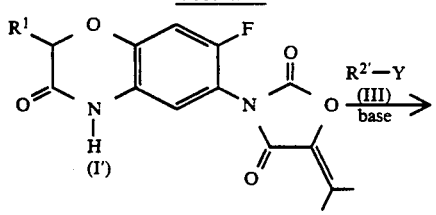

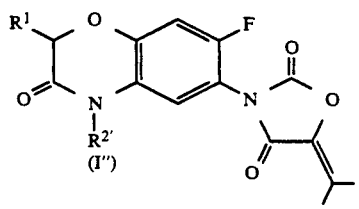

wherein $R^1$ is as defined above, $R^{2'}$ represents an alkyl group, a cyanoalkyl group, an alkenyl group, an alkynyl group or an aralkyl group, $R^3$ represents a hydrogen atom or a lower alkyl group, and Y represents a leaving group.

The procedure of Process 1 is hereinafter described in more detail.

That is, a benzoxazinone compound represented by the formula (I'), i.e., a compound having the formula (I) wherein $R^2$ represents a hydrogen atom, can be prepared by reducing the nitro group of the oxazolidinedione compound represented by the formula (II) with a reducing agent, for example, reduced iron, in acetic acid, and then condensing the resulting amino group with the acid or ester group. The reaction is preferably carried out in acetic acid, but other solvents such as a mixed solvent thereof, e.g., a mixture of acetic acid and ethyl acetate, can be used. The reaction temperature can be in the range of from room temperature (about 15° C. to 30° C.) to about 150° C., but the reaction is preferably carried out at the refluxing temperature of the solvent used. After completion of the reaction, the desired product can be isolated as crystals from the reaction mixture by a conventional treatment, such as concentration, extraction with a solvent, etc., and, if desired, can be further purified by silica gel column chromatography or recrystallization.

A benzoxazinone compound represented by the formula (I''), i.e., a compound having the formula (I) wherein $R^2$ represents the group other than the hydrogen atom, can be easily prepared by reacting the benzoxazinone compound represented by the formula (I') with a compound represented by the formula $R^{2'}—Y$ (III) wherein $R^{2'}$ and Y are as defined above, in the presence of a base, to introduce the group $R^{2'}$ on the nitrogen atom of the compound represented by the formula (I'). Examples of the cleaving group Y include a halogen atom such as chlorine atom, bromine atom, iodine atom, etc., and a substituted sulfornyloxy group such as tolylsulfonyloxy group, phenylsulfonyloxy group, methylsulfonyloxy group, etc. The reaction is preferably carried out in an organic solvent, and examples of the organic solvent include tetrahydrofuran, diethyl ether, dimethoxyethane, dimethylformamide, dimethyl sulfoxide, acetonitrile, propionitrile, acetone, methyl ethyl ketone, benzene, toluene, etc. Examples of the base which can be used include an alkyl lithium such as n-butyl lithium, secbutyl lithium and methyl lithium, an alkali metal hydride such as sodium hydride and potassium hydride, and an organic or inorganic base such as sodium carbonate, potassium carbonate, sodium hydrogencarbonate, sodium acetate, potassium acetate, sodium hydroxide, potassium hydroxide and calcium hydroxide, and the like. The reaction temperature varies depending upon the type of base and solvent used, but is generally in the range of from about −78° C. to about 150° C. After completion of the reaction, the desired product can be isolated as crystals from the reaction mixture by a conventional treatment, such as concentration, extraction with a solvent, etc., and, if desired, can be further purified by silica gel column chromatography or recrystallization.

The oxazolidinedione compounds represented by the formula (II) used as starting materials for the preparation of the benzoxazinone compounds of the formula (I) of the present invention can be prepared by the following process:

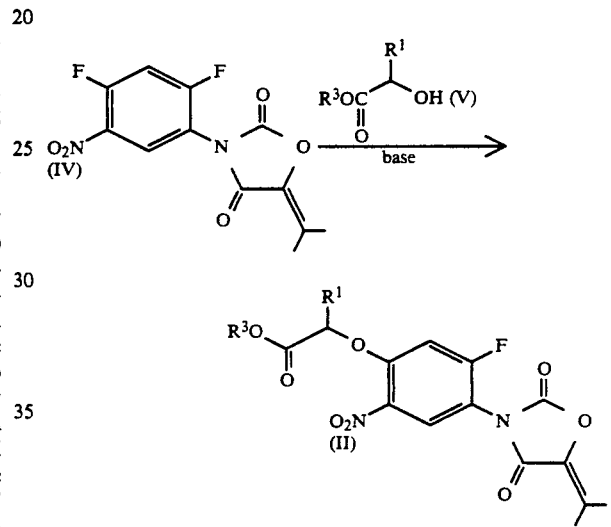

wherein $R^1$ and $R^3$ are as defined above.

More specifically, a compound of the formula (II) can be prepared by reacting an oxazolidinedione compound represented by the formula (IV), which can be prepared by a known method as described in Japanese Patent Application (Kokai) No. 174065/87, with a 2-hydroxycarboxylic acid or an ester thereof represented by the formula (V) in the presence or absence of an organic solvent and in the presence of a base. Examples of the base which can be used in this reaction include a tertiary aliphatic or aromatic amine compound such as triethylamine, tributylamine, N-methylmorpholine, pyridine and lutidine, and an organic or inorganic base such as potassium carbonate, sodium carbonate, sodium acetate, potassium acetate, sodium amide, and the like. The reaction can be carried out in the absence of a solvent or in the presence of a generally used organic solvent. Further, the reaction can be carried out efficiently under a pressurized condition. The 2-hydroxycarboxylic acids or the esters thereof represented by the formula (V) used as a starting material can be prepared easily from commercially available compounds, and examples of compounds of the formula (V) include glycolic acid, lactic acid, 2-hdroxyvaleric acid, 2-hydroxy-3-methylpentanoic acid, methyl glycolate, ethyl glycolate, butyl glycolate, methyl lactate, ethyl lactate, butyl lactate, methyl 2-hydroxyvalerate, methyl 2-hydroxyisovalerate, methyl 2-hydroxy-3-methylpentanoate, methyl 2-hydroxy-4-methylpentanoate, methyl 2-hydroxyhexanoate, methyl 2-hydroxy-3-methylheptanoate, and the like.

Process 2

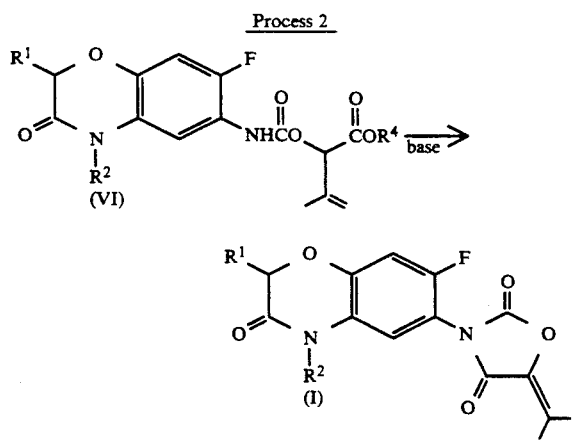

wherein $R^1$ and $R^2$ are as defined above, and $R^4$ represents a lower alkyl group.

The procedure of Process 2 is hereinafter described in more detail.

That is, the benzoxazinone compound represented by the formula (I) according to the present invention can be easily prepared by treating a carbamic ester represented by the formula (VI) with a base. The reaction is preferably carried out in a conventional organic solvent at room temperature or under reflux. Examples of the base which can be used include a tartiary amine such as triethylamine, tripropylamine, tributylamine, N-methylmorpholine and dimethylaniline, an aromatic amine such as pyridine, lutidine and pyrimidine, an alkali metal alkoxide such as sodium methoxide, sodium ethoxide, potassium t-butoxide, an alkali metal hydride such as sodium hydride and potassium hydride, an inorganic base such as sodium carbonate, potassium carbonate, sodium hydroxide and potassium hydroxide, a carboxylic acid alkali metal salt such as sodium acetate and potassium acetate, and the like. The amount of the base used is not limited and a catalytic amount of the base is generally sufficient.

The carbamic ester represented by the formula (VI) used as a starting material can be prepared according to the reaction scheme shown below by converting the amino group of known aminobenzoxazinone compounds of the formula (VII) described in, for example, Japanese Patent Application (Kokai) No. 76486/86 into an isocyanate group or a chlorocarbamoyl group using phosgene or phosgene dimer, and reacting the resulting compound of the formula (VIII) with a 2-hydroxy-3-methyl-3-butenoic ester represented by the formula (IX), optionally in the presence of a base.

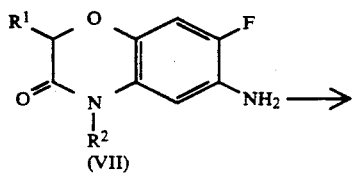

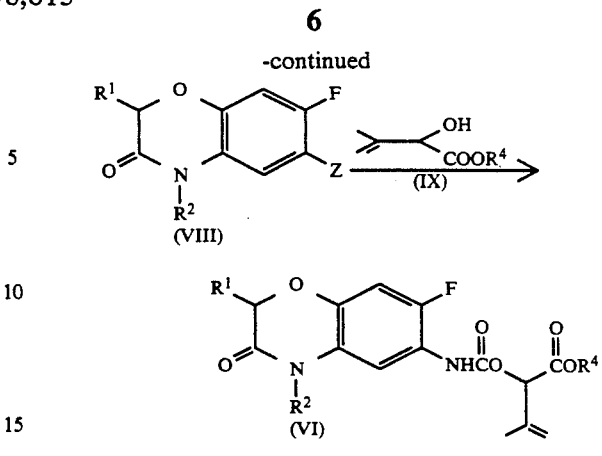

wherein $R^1$, $R^2$ and $R^4$ are as defined above, and Z represents an isocyanate group or a chlorocarbamoyl group.

In carrying out the reaction of Process 2, the desired benzoxazinone compounds represented by the formula (I) can be prepared by treating the carbamic ester of the formula (VI) with a base, without isolating the ester (VI) from the reaction mixture obtained by the reaction between the compound of formula (VIII) and the 2-hydroxy-3-methylbutenoic ester of the formula (IX). After completion of the reaction, the desired benzoxazinone compound can be purified by column chromatography, or easily isolated in a substantially pure form by adding an appropriate solvent, for example, methyl alcohol, ethyl alcohol, diethyl ether, hexane or the like, to the reaction mixture, optionally with cooling, and separating the precipitated crystals by filtration.

In the benzoxaxinone compounds represented by the formula (I) prepared as described above, the alkyl group represented by $R^1$ and $R^2$ has 1 to 8 carbon atoms, preferably 1 to 4 carbon atoms, and examples of the alkyl group include methyl group, ethyl group, propyl group, isopropyl group, butyl group, isobutyl group, sec-butyl group, tert-butyl group, pentyl group, isopentyl group, hexyl group, isohexyl group, and the like. The cyanoalkyl group represented by $R^2$ has 1 to 4 carbon atoms, preferably 1 to 2 carbon atoms, in the alkyl moiety thereof. The cyano group of the cyanoalkyl group may be substituted on a terminal carbon atom or any other carbon atom of the alkyl group, and examples of the cyanoalkyl group include cyanomethyl group, 1-cyanoethyl group, 2-cyanoethyl group, 3-cyanopropyl group, and the like. The alkenyl group represented by $R^2$ has 3 to 6 carbon atoms, preferably 3 to 4 carbon atoms, and examples of the alkenyl group include an alkyl group, methallyl group, crotyl group, 1-methylallyl group, prenyl group, 3-methyl-3-butenyl group, 3-pentenyl group, and the like. The alkynyl group represented by $R^2$ has 3 to 6 carbon atoms, preferably 3 to 4 carbon atoms, and examples of the alkynyl group include a propargyl group, 1-methylpropargyl group, 1-ethylpropargyl group, 2-butynyl group, 1-methyl-2-butynyl group, 3-pentynyl group, 3-butynyl group, 2-pentynyl group, and the like. The aralkyl group represented by $R^2$ has 7 to 10 carbon atoms, preferably 7 to 8 carbon atoms, and the aryl moiety thereof may be unsubstituted or substituted with a halogen atom, a lower alkyl group, etc. Examples of the aralkyl group include benzyl group, phenethyl group, p-fluorobenzyl group, p-chlorobenzyl group, and the like.

Typical examples of the benzoxazinone compounds according to the present invention are shown in Table 1 below, but the present invention is not limited to these specific examples.

TABLE 1

[Structure with $R^1$, $R^2$, F substituents]

| Compound No. | $R^1$ | $R^2$ | Example No. |
|---|---|---|---|
| 1 | H | H | 1 and 16 |
| 2 | $CH_3$ | H | 2 |
| 3 | H | $CH_3$ | 3 |
| 4 | H | $CH_3(CH_2)_4CH_2$ | 4 |
| 5 | H | $H_2C=CHCH_2$ | 5 |
| 6 | H | $C_6H_5CH_2$ | 6 |
| 7 | H | trans-$CH_3CH=CHCH_2$ | 7 |
| 8 | H | $HC\equiv CCH_2$ | 8 |
| 9 | $CH_3$ | $CH_3$ | 9 |
| 10 | $CH_3$ | $CH_3(CH_2)_4CH_2$ | 10 |
| 11 | $CH_3$ | $H_2C=CHCH_2$ | 11 |
| 12 | $CH_3$ | $HC\equiv CCH_2$ | 12 |
| 13 | H | $(CH_3)_2CH$ | 13 |
| 14 | H | $NCCH_2$ | 14 |
| 15 | H | NCCH<br>\|<br>$CH_3$ | 15 |
| 16 | $(CH_3)_2CH$ | H | 17 |

The preparation of the compounds according to the present invention is illustrated by the following Examples, but the present invention is not limited thereto.

EXAMPLE 1

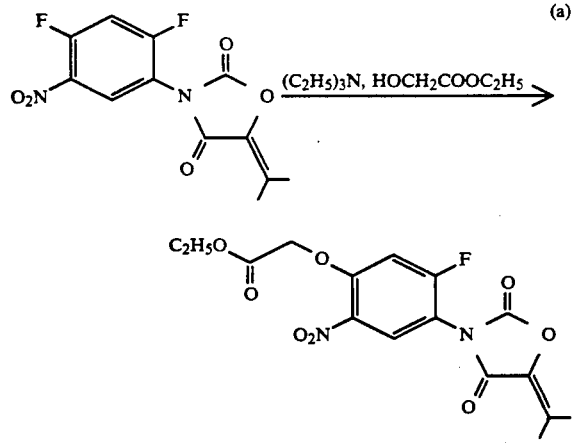

4.1 g (13.6 mmol) of 3-(2,4-difuoro-5-nitrophenyl)-5-isopropylidene-1,3-oxazolidine-2,4-dione and 20 ml of ethyl glycolate were charged in a 100 cc round-bottom flask, and 4 ml of triethylamine was added dropwise thereto while stirring at room temperature. After stirring the mixture at room temperature overnight, 1N hydrochloric acid was added to the reaction mixture. The resulting mixture was extracted with ethyl acetate (20 ml×3), and the organic layer was washed with water (10 ml×3). The ethyl acetate solution thus obtained was dried over anhydrous magnesium sulfate. The drying agent was filtered off, and the solvent was removed by distillation under reduced pressure from the filtrate to give 6.5 g of a yellow oily product. The product was purified by silica gel column chromatography to give 3.68 g of a white product. The product was confirmed to be 3-(2-fluoro-4-ethoxycarbonylmethyloxy-5-nitrophenyl)-5-isopropylidene-1,3-oxazolidine-2,4-dione from the analytical data of $^1$H-NMR and IR spectra, etc.

$^1$H-NMR (CDCl$_3$): δ1.28 (3H, t, J=7.5 Hz), 2.03 (3H, s), 2.26 (3H, s), 4.25 (2H, q, J=7.5 Hz), 4.78 (2H, s), 6.88 (1H, d, $J_{HF}$=11.1 Hz), 8.00 (1H, d, $J_{HF}$=7.5 Hz), ppm.

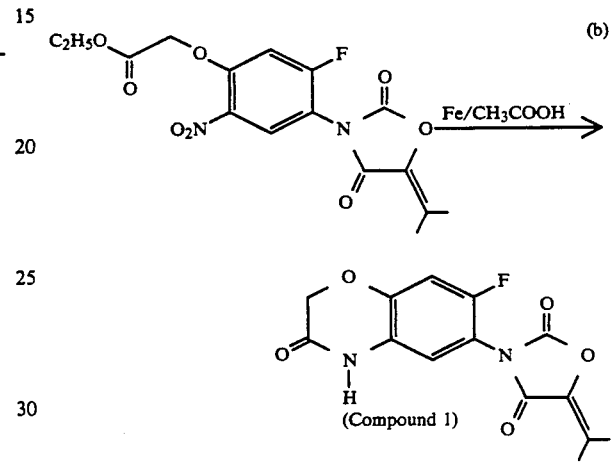

6.8 g of reduced iron was placed in a 300 cc 3-necked flask equipped with a mechanical stirrer, a dropping funnel and a reflux condenser, and then 20 ml of acetic acid was added thereto. The mixture was heated under reflux until the mixture turned into a white suspension. A solution of 2.76 g (7.2 mmol) of 3-(2-fluoro-4-ethoxycarbonylmethyloxy-5-nitrophenyl)-5-isopropylidene-1,3-oxazolidine-2,4-dione obtained in (a) above in 10 ml of ethyl acetate was added dropwise to the suspension under reflux. After completion of the addition, the mixture was stirred for an additional one hour under reflux, and, after cooling, insoluble materials in the mixture were removed by filtration. 50 ml of 1N hydrochloric acid was added to the resulting solution, and the mixture was extracted with ethyl acetate (50 ml×3). The organic layer was washed with water (10 ml×3) and dried over anhydrous magnsium sulfate. The drying agent was removed, and the solvent was distilled off under reduced pressure to give 2.1 g of a pale brown solid. The product was confirmed to be 3-(7-fluoro-2H-1,4-benzoxazine-3(4H)-one-6-yl)-5-isopropylidene-1,3-oxazolidine-2,4-dione (Compound 1) from the analytical data of $^1$H-NMR and IR spectra, etc.

EXAMPLE 2

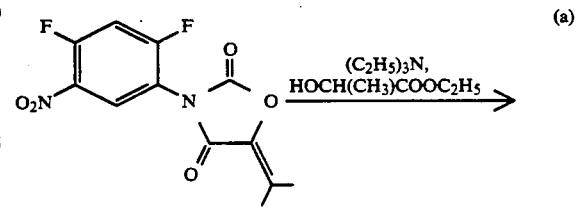

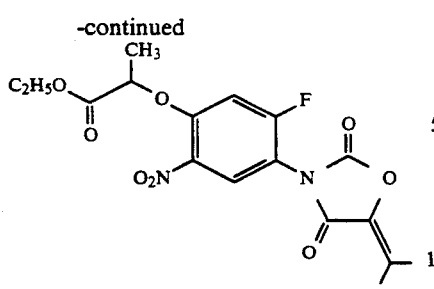

3.0 g (10 mmol) of 3-(2,4-difluoro-5-nitrophenyl)-5-isopropylidene-1,3-oxazolidine-2,4-dione and 15 ml of (−)-ethyl lactate were charged into a 100 cc round-bottom flask, and 4 ml of triethylamine was added dropwise thereto while stirring at room temperature. After stirring the mixture overnight at room temperature, 1N hydrochloric acid was added to the reaction mixture. The resulting mixture was extracted with ethyl acetate (10 ml×3), and the organic layer was washed with water (5 ml×3). The resulting ethyl acetate solution was dried over anhydrous magnesium sulfate. After filtering off the drying agent, the solvent was distilled off from the filtrate to give 5.7 g of a yellow oily product. The product was recrystallized from ethyl acetate-hexane to give 1.16 g of a product as a yellow transparent solid. Further recrystallization from the mother liquor yielded 752 mg of a yellow solid product. The product was confirmed to be (+)-3-[2-fluoro-4-(1-ethoxycarbonyl)ethyloxy-5-nitrophenyl]-5-isopropylidene-1,3-oxazolidine-2,4-dione from the analytical data of $^1$H-NMR and IR spectra, etc.

$^1$H-NMR (CDCl$_3$): δ1.27 (3H, t, J=6.6 Hz), 1.71 (3H, d, J=6.3 Hz), 2.06 (3H, s), 2.28 (3H, s), 4.23 (2H, q, J=6.6 Hz), 4.82 (1H, q, J=6.3 Hz), 6.82 (1H, d, J$_{HF}$=11.1 Hz), 8.31 (1H, d, J$_{HF}$=8.1 Hz), ppm (b)

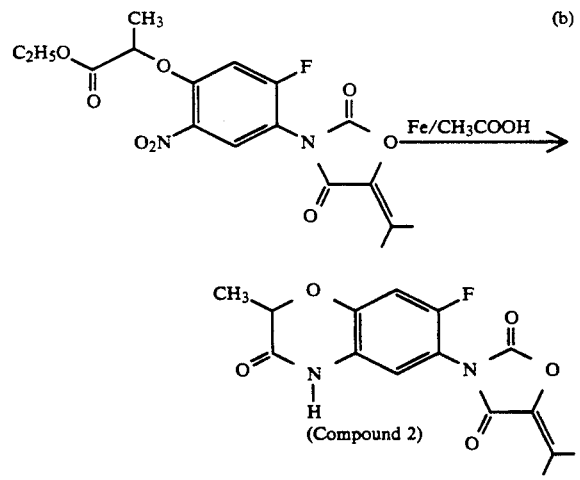

(Compound 2)

3.8 g of reduced iron was charged into a 300 cc 3-necked flask equipped with a mechanical stirrer, a dropping funnel and a reflux condenser, and then 30 ml of acetic acid was added thereto. The mixture was heated under reflux until the mixture turned into a white suspension. A solution of 1.1 g (2.8 mmol) of (+)-3-[2-fluoro-4-(1-ethoxycarbonyl)-ethyloxy-5-nitrophenyl]-5-isopropylidene-1,3-oxazolidine-2,4-dione obtained in (a) above in 20 ml of ethyl acetate was added dropwise to the suspension under reflux. After completion of the reaction, the mixture was stirred for an additional one hour under reflux, and, after cooling, insoluble materials in the mixture were removed by filtration. 50 ml of 1N hydrochloric acid was added to the resulting solution, and the mixture was extracted with ethyl acetate (50 ml×3). The organic layer was washed with water (10 ml×3) and dried over anhydrous magnesium sulfate. The solvent was distilled off under reduced pressure to give 0.91 g of a pale brown solid. The product was confirmed to be (+)-3-(7-fluoro-2-methyl-2H-1,4-benzoxazine-3-(4H)-one-6-yl)-5-isopropylidene-1,3-oxazolidine-2,4-dione (Compound 2) from the analytical data of $^1$H-NMR and IR specra, etc.

EXAMPLE 3

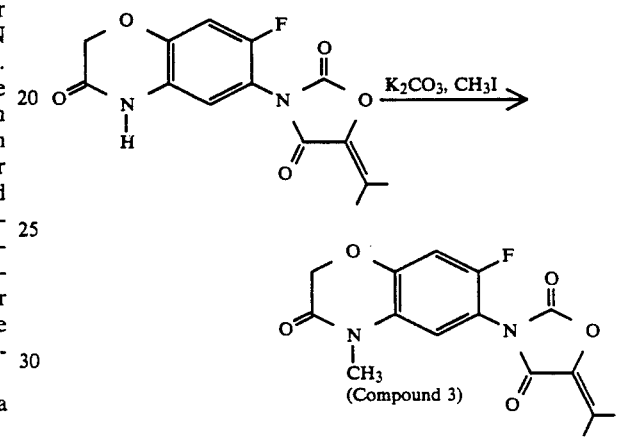

(Compound 3)

130 mg (0.42 mmol) of 3-(7-fluoro-2H-1,4-benzoxazine-3(4H)-one-6-yl)-5-isopropylidene-1,3-oxazolidine-2,4-dione and 130 mg of potassium carbonate were charged into a 25 cc round-bottom flask and dissolved in 5 ml of N,N-dimethylformamide. Then, 500 μl of methyl iodide was added dropwise to the solution while stirring at room temperature. The mixture was then stirred for 3 hours at room temperature. After completion of the reaction, 1N hydrochloric acid was added thereto, and the mixture was extracted with ethyl acetate (2 ml×3). The organic layer was washed with water (1 ml×3) and dried over anhydrous magnesium sulfate. The drying agent was filtered off, and the filtrate was concentrated under reduced pressure to give 250 mg of a brown oily product. The product was purified by silica gel column chromatography to give 123 mg of a white solid. The product was confirmed to be 3-(7-fluoro-4-methyl-2H-1,4-benzoxazine-3(4H)-one-6-yl)-5-isopropylidene-1,3-oxazolidine-2,4-dione (Compound 3) from the analytical data of $^1$H-NMR and IR spectra, etc.

EXAMPLE 4

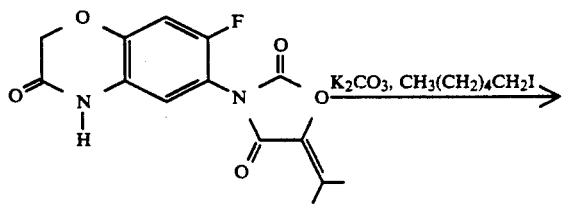

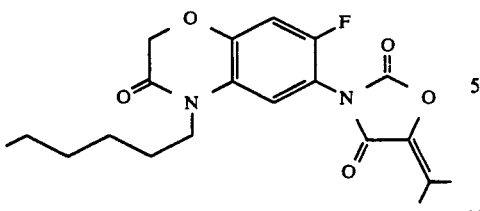

200 mg (0.65 mmol) of 3-(7-fluoro-2H-1,4-benzoxazine-3(4H)-one-6-yl)-5-isopropylidene-1,3-oxazolidine-2,4-dione and 200 mg of potassium carbonate were charged into a 25 cc round-bottom flask and dissolved in 2 ml of N,N-dimethylformamide. Then, 500 μl of hexyl iodide was added dropwise to the solution while stirring at room temperature. The mixture was stirred at room temperature for 5 hours. After completion of the reaction, 1N hydrochloric acid was added thereto, and the mixture was extracted with ethyl acetate (2 ml×3). The organic layer was washed with water (1 ml×3) and dried over anhydrous magnesium sulfate. After filtering off the drying agent, the filtrate was concentrated under reduced pressure to give 102 mg of a brown oily product. The product was purified by silica gel column chromatography to give 79 mg of a white solid. The product thus obtained was confirmed to be 3-(7-fluoro-4-hexyl-2H-1,4-benzoxazine-3(4H)-one-6-yl)-5-isopropylidene-1,3-oxazolidine-2,4-dione (Compound 4) from the analytical data of $^1$H-NMR and IR spectra, etc.

EXAMPLE 5

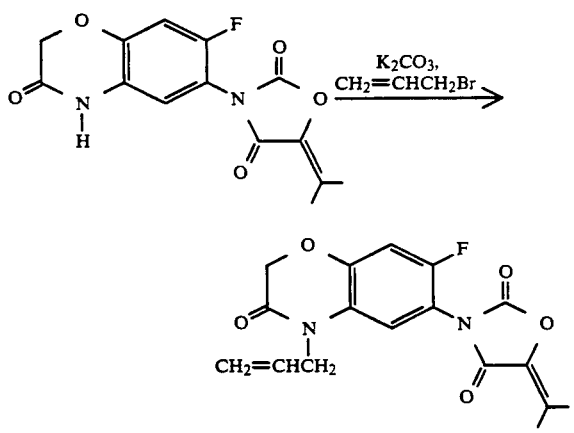

200 mg (0.64 mmol) of 3-(7-fluoro-2H-1,4-benzoxazine-3(4H)-one-6-yl)-5-isopropylidene-1,3-oxazolidine-2,4-dione and 200 mg of potassium carbonate were charged into a 25 cc round-bottom flask and dissolved in 5 ml of N,N-dimethylformamide. Then, 500 μl of allyl bromide was added dropwise thereto while stirring at room temperature. The resulting mixture was stirred at room temperature for 4 hours. After completion of the reaction, 1N hydrochloric acid was added to the reaction mixture, and the mixture was extracted with ethyl acetate (2 ml×3). The organic layer was washed with water (1 ml×3) and dried over anhydrous magnesium sulfate. After filtering off the drying agent, the resulting solution was concentrated under reduced pressure to give 138 mg of a brown oily product. The product was purified by silica gel column chromatography to give 97 mg of a white solid. The product thus obtained was confirmed to be 3-(4-allyl-7-fluoro-2H-1,4-benzoxazine-3(4H)-one-6-yl)-5-isopropylidene-1,3-oxazolidine-2,4-dione (Compound 5) from the analytical data of $^1$H-NMR and IR spectra, etc.

EXAMPLE 6

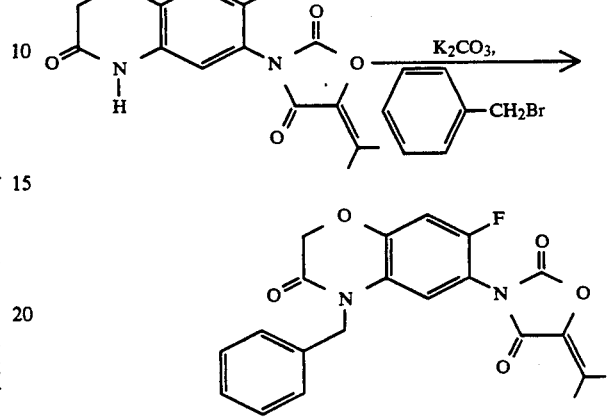

200 mg (0.64 mmol) of 3-(7-fluoro-2H-1,4-benzoxazine-3(4H)-one-6-yl)-5-isopropylidene-1,3-oxazolidine-2,4-dione and 200 mg of potassium carbonate were charged into a 25 cc round-bottom flask and dissolved in 2 ml of N,N-dimethylformamide. Then, 500 μl of benzyl bromide was added dropwise to the solution while stirring, and the mixture was stirred for 6 hours at room temperature. After completion of the reaction, 1N hydrochloric acid was added thereto, and the mixture was extracted with ethyl acetate (2 ml×3). The organic layer was washed with water (1 ml×3) and dried over anhydrous magnesium sulfate. The drying agent was filtered off, and the resulting solution was concentrated under reduced pressure to give 240 mg of a brown oily product. The product was purified by silica gel column chromatography to give 153 mg of a white solid. The product was confirmed to be 3-(4-benzyl-7-fluoro-2H-1,4-benzolidine-3(4H)-one-6-yl)-5-isopropylidene-1,3-oxazolidine-2,4-dione (Compound 6) from the anlytical data of $^1$H-NMR and IR spectra, etc.

EXAMPLE 7

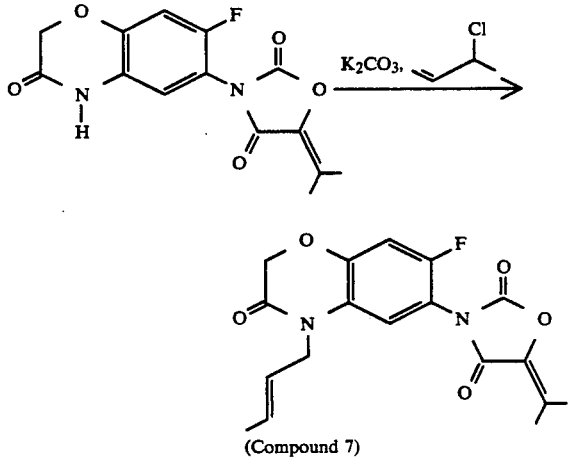

(Compound 7)

200 mg (0.64 mmol) of 3-(7-fluoro-2H-1,4-benzoxazine-3(4H)-one-6-yl)-5-isopropylidene-1,3-oxazolidine-2,4-dione and 200 mg of potassium carbonate were charged into a 25 cc round-bottom flask and dissolved in 2 ml of N,N-dimethylformamide. Then, 600 μl of 3-chloro-1-butene was added dropwise to the solution while stirring at room temperature, and the resulting mixture was stirred at room temperature for 12 hours. After completion of the reaction, 1N hydrochloric acid was added to the reaction mixture, and the resulting mixture was extracted with ethyl acetate (2 ml×3). The organic layer was washed with water (1 ml×3) and dried over anhydrous magnesium sulfate. The drying agent was filtered off, and the resulting solution was concentrated under reduced pressure to give 105 mg of a brown oily product. The product was purified by silica gel column chromatography to give 74 mg of a white solid. The product thus obtained was confirmed to be 3-[4-(E)-crotyl-7-fluoro-2H-1,4-benzoxazine-3(4H)-one-6-yl]-5-isopropylidene-1,3-oxazolidine-2,4-dione (Compound 7) from the analytical data of $^1$H-NMR and IR spectra, etc.

EXAMPLE 8

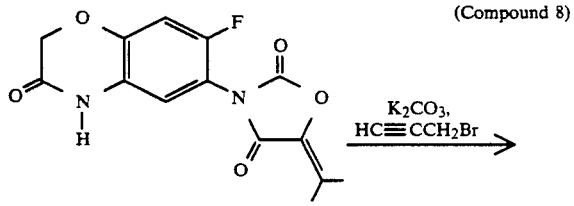

(Compound 8)

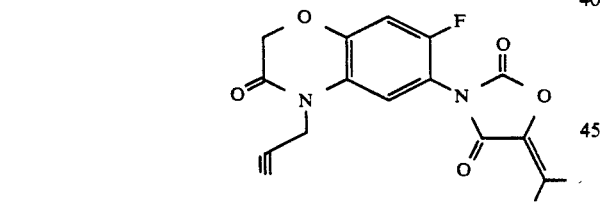

347 mg (1.13 mmol) of 3-(7-fluoro-2H-1,4-benzoxazine-3(4H)-one-6-yl)-5-isopropylidene-1,3-oxazolidine-2,4-dione and 100 mg of potassium carbonate were charged into a 25 cc round-bottom flask and dissolved in 30 ml of N,N-dimethylformamide. Then, 200 μl of propargyl bromide was added dropwise thereto while stirring at room temperature, and the mixture was stirred for 5 hours at room temperature. After completion of the reaction, 1N hydrochloric acid was added to the reaction mixture. The resulting mixture was allowed to stand at room temperature, and the precipitated crystals (345 mg) were isolated by filtration. The product thus obtained was confirmed to be 3-(7-fluoro-4-propargyl-2H-1,4-benzoxazine-3(4H)-one-6-yl)-5-isopropylidene-1,3-oxazolidine-2,4-dione (Compound 8) from the analytical data of $^1$H-NMR and IR spectra, etc.

EXAMPLE 9

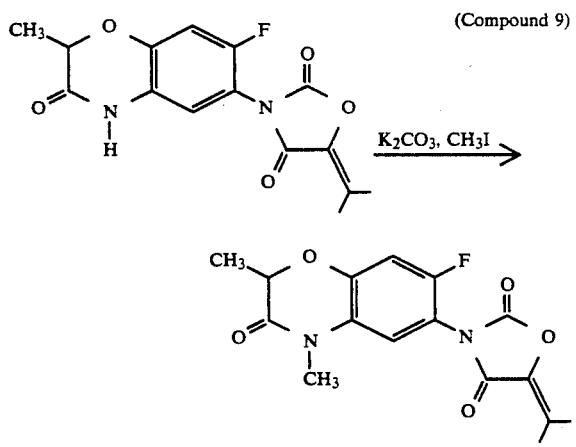

(Compound 9)

200 mg (0.62 mmol) of (+)-3-(7-fluoro-2-methyl-2H-1,4-benzoxazine-3(4H)-one-6-yl)-5-isopropylidine-1,3-oxazolidine-2,4-dione and 200 mg of potassium carbonate were charged into a 25 cc round-bottom flask and dissolved in 2 ml of N,N-dimethylformamide. Then, 500 μl of methyl iodide was added dropwise to the solution while stirring at room temperature, and the resulting mixture was stirred at room temperature for 3 hours. After completion of the reaction, 1N hydrochloric acid was added to the reaction mixture. The resulting mixture was allowed to stand at room temperature, and the precipitated crystals (184 mg) were isolated by filtration. The product thus obtained was confirmed to be (+)-3-(7-fluoro-2,4-dimethyl-2H-1,4-benzoxazine-3(4H)-one-6-yl)-5-isopropylidene-1,3-oxazolidine-2,4-dione (Compound 9) from the analytical data of $^1$H-NMR and IR spectra, etc.

EXAMPLE 10

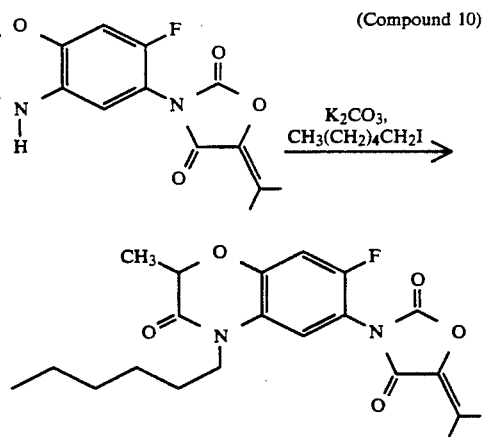

(Compound 10)

123 mg (0.4 mmol) of (+)-3-(7-fluoro-2-methyl-2H-1,4-benzoxazine-3(4H)-one-6-yl)-5-isopropylidene-1,3-oxazolidine-2,4-dione and 130 mg of potassium carbonate were charged into a 25 cc round-bottom flask and dissolved in 4 ml of N,N-dimethylformamide. 500 μl of hexyl iodide was added to the solution while stirring at room temperature and the resulting mixture was stirred for 3 hours at room temperature. After completion of the reaction, 1N hydrochloric acid was added thereto, and the mixture was extracted with ethyl acetate (3 ml×3). The organic layer was washed with water (2 ml×3), and dried over anhydrous magnesium sulfate. The drying agent was filtered off and then the resulting solution was concentrated under reduced pressure to give 108 mg of a brown oily product. The product was purified by silica gel column chromatography to give 81 mg of a white solid. The product thus obtained was confirmed to be (+)-3-(7-fluoro-4-hexyl-2-methyl-2H-1,4-benzoxazine-3(4H)-one-6-yl)-5-isopropylidene-1,3-oxazolidine-2,4-dione (Compound 10) from the analytical data of $^1$H-NMR and IR spectra, etc.

EXAMPLE 11

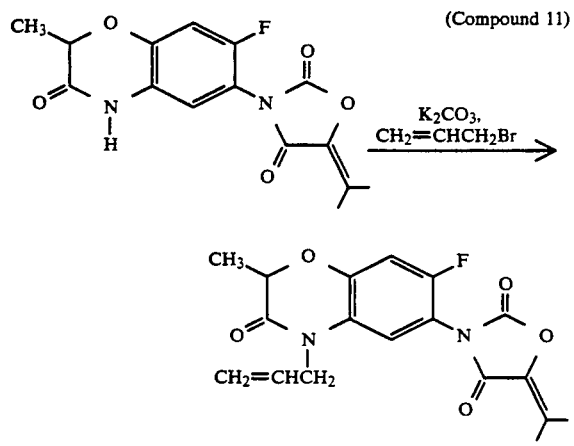

(Compound 11)

200 mg (0.62 mmol) of (+)-3-(7-fluoro-2-methyl-2H-1,4-benzoxazine-3(4H)-one-6-yl)-5-isopropylidene-1,3-oxazolidine-2,4-dione and 200 mg of potassium carbonate were charged into a 25 cc of round-bottom flask and dissolved in 2 ml of N,N-dimethylformamide. 500 μl of allyl bromide was added dropwise to the solution while stirring, and the resulting mixture was stirred for 3 hours at room temperature. After completion of the reaction, 1N hydrochloric acid was added thereto, and the mixture was extracted with ethyl acetate (3 ml×3). The organic layer was washed with water (2 ml×3) and dried over anhydrous magnesium sulfate. The drying agent was filtered off, and the resulting solution was concentrated under reduced pressure to give 252 mg of a brown oily product. The product was purified by silica gel column chromatography to give 173 mg of a white solid. The product thus obtained was confirmed to be (+)-3-(4-allyl-7-fluoro-2-methyl-2H-1,4-benzoxazine-3(4H)-one-6-yl)-5-isopropylidene-1,3-oxazolidine-2,4-dione (Compound 11) from the analytical data of $^1$H-NMR and IR spectra, etc.

EXAMPLE 12

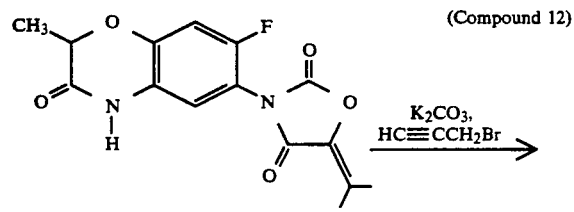

(Compound 12)

-continued

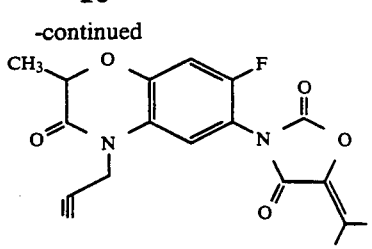

163 mg (0.51 mmol) of (+)-3-(7-fluoro-2-methyl-2H-1,4-benzoxazine-3(4H)-one-6-yl)-5-isopropylidene-1,3-oxazolidine-2,4-dione and 140 mg of potassium carbonate were charged into a 25 cc round-bottom flask and dissolved in 5 ml of N,N-dimethylformamide. 300 μl of propargyl bromide was added dropwise thereto while stirring at room temperature. The mixture was then stirred at room temperature for 5 hours. After completion of the reaction, 1N hydrochloric acid was added thereto, and the mixture was allowed to stand at room temperature. The precipitated crystals (167 mg) were isolated by filtration and confirmed to be (+)-3-(7-fluoro-2-methyl-4-propargyl-2H-1,4-benzoxazine-3(4H)-one-6-yl)-5-isopropylidene-1,3-oxazolidine-2,4-dione (Compound 12) from the analytical data of $^1$H-NMR and IR spectra, etc.

EXAMPLE 13

(a)

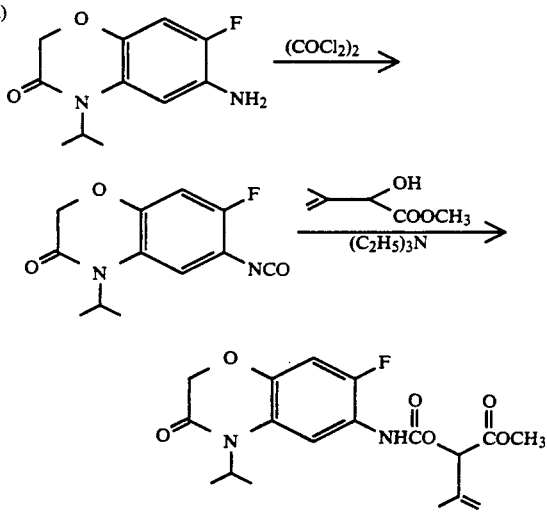

3.24 g (14.0 mmol) of 6-amino-7-fluoro-4-isopropyl-2H-1,4-benzoxazine-3(4H)-one was charged into a 100 cc round-bottom flask and dissolved in 100 ml of ethyl acetate. 5.0 ml of phosgene dimer (trichloromethyl chloroformate) was added thereto, and, while heating the mixture under reflux, ethyl acetate was distilled off until the mixture reached to a volume of about 10 ml. After cooling the mixture to room temperature, 30 ml of carbon tetrachloride was added and a small amount of the solid deposited was removed by filtration. The solvent was distilled off from the filtrate under reduced pressure. The resulting pale brown solid was confirmed to be substantially pure 7-fluoro-6-isocyanato-4-isopropyl-2H-1,4-benzoxazine-3(4H)-one from $^1$H-NMR spectrum. Then, 3.4 g (13.6 mmol) of the isocyanate thus obtained and 2.3 g (17.7 mmol) of methyl 2-hydroxy-3-methyl-3-butenoate were charged into a 200 cc round-bottom flask and dissolved in diethyl ether (70 ml) and tetrahydrofuran (25 ml). Thereafter, 2.5 ml of triethylamine was added thereto, and the solution was stirred at room temperature for 2 hours. After completion of the reaction, the solution was washed with 1N hydrochloric acid, and the organic layer was dried over anhydrous magnesium sulfate. The drying agent was filtered off, and the filtrate was concentrated under reduced pressure to give a pale yellow oily product. The product was purified by silica gel column chromatography to give 2.99 g of a colorless oily product. The product thus obtained was confirmed to be methyl 2-[N-7-fluoro-4-isopropyl-2H-1,4-benzoxazine-3(4H)-one-6-yl)carbamoyloxy]-3-methyl-3-butenoate from the analytical date of $^1$H-NMR and IR spectra, etc.

$^1$H-NMR (CDCl$_3$): δ1.51 (6H, d, J=6.9 Hz), 1.82 (3H, s), 3.68 (3H, s), 4.45 (2H, s), 4.75 (1H, sep, J=6.9 Hz), 5.14 (1H, brs), 5.22 (1H, brs), 5.51 (1H, s), 6.76 (1H, d, J$_{HF}$=10.8 Hz), 7.03 (1H, br), 7.97 (1H, d, J$_{HF}$=8.1 Hz), ppm.

(b) (Compound 13)

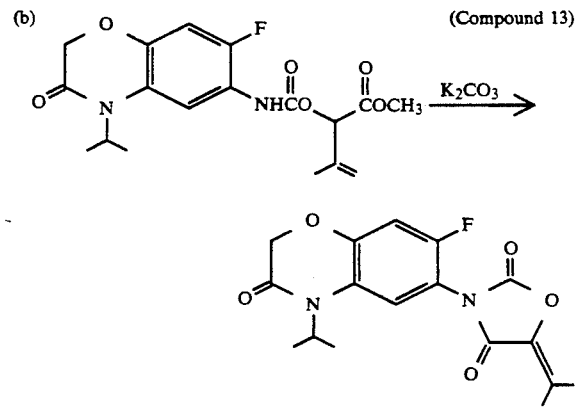

1.48 g (3.89 mmol) of methyl 2-[N-(7-fluoro-4-isopropyl-2H-1,4-benzoxazine-3(4H)-one-6-yl)carbamoyloxy]-3-methyl-3-butenoate and 537 mg (3.89 mmol) of potassium cabonate were charged into 100 cc roundbottom flask and dissolved in 45 ml of acetonitrile. The solution was stirred at room temperature for 12 hours and, after adding 1N hydrochloric acid thereto, the mixture was extracted with ethyl acetate (15 ml×3). The organic layer was washed with water (7 ml×3) and dried over anhydrous magnesium sulfate. The drying agent was filtered off, and the filtrate was concentrated under reduced pressure to give a pale yellow oily product. The product thus obtained was recrystallized from methanol to give 923 mg of a white solid. The product was confirmed to be 3-(7-fluoro-4-isopropyl-2H-1,4-benzoxazine-3(4H)-one-6-yl)-5-isopropylidene-1,3-oxazolidine-2,4-dione (Compound 13) from the analytical date of $^1$H-NMR and IR spectra, etc.

EXAMPLE 14

(Compound 14)

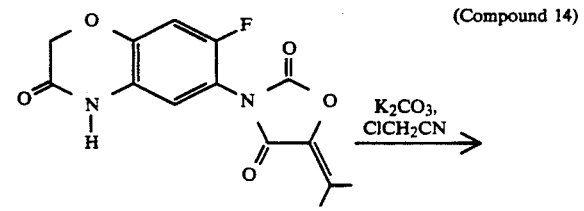

-continued

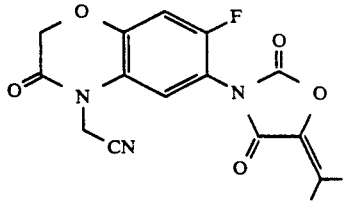

500 mg (1.63 mmol) of 3-(7-fluoro-2H-1,4-benzoxazine-3(4H)-one-6-yl)-5-isopropylidene-1,3-oxazolidine-2,4-dione and 500 mg of potassium carbonate were charged into a 25 cc round-bottom flask and dissolved in 5 ml of N,N-dimethylformamide. 135 mg of chloroacetonitrile was added dropwise to the solution while stirring, and the solution was stirred for 3 hours at room temperature. After completion of the reaction, 1N hydrochloric acid was added thereto, and the mixture was extracted with ethyl acetate (5 ml×3). The organic layer was washed with water (2 ml×3) and dried over anhydrous magnesium sulfate. The drying agent was filtered off, and the resulting solution was concentrated under reduced pressure to give 511 mg of a pale yellow oily product. The product was purified by silica gel column chromatography to give 353 mg of a white solid. The product thus obtained was confirmed to be 3-(4-cyanomethyl-7-fluoro-2H-1,4-benzoxazine-3(4H)-one-6-yl)-5-isopropylidene-1-3,-oxazolidine-2,4-dione (Compound 14) from the analytical data of $^1$H-NMR and IR spectra, etc.

EXAMPLE 15

(Compound 15)

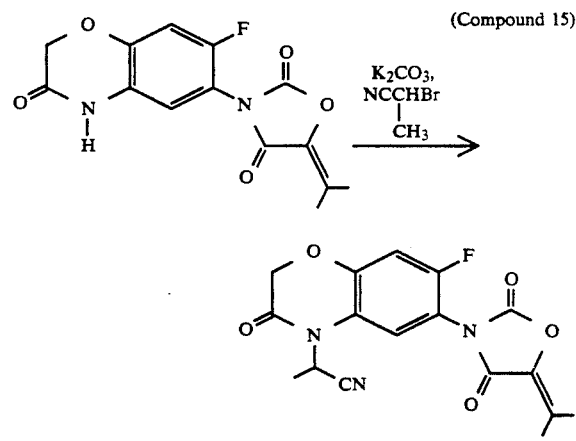

400 mg (0.31 mmol) of 3-(7-fluoro-2H-1,4-benzoxazine-3(4H)-one-6-yl)-5-isopropylidene-1,3-oxazolidine-2,4-dione and 400 mg of potassium carbonate were charged into a 25 cc round-bottom flask and dissolved in 4 ml of N,N-dimethylformamide. Then, 350 mg of 2-bromopropionitrile was added dropwise to the solution while stirring at room temperature, and the solution was stirred for 24 hours at room temperature. After completion of the reaction, 1N hydrochloric acid was added thereto, and the resulting mixture was extracted with ethyl acetate (4 ml×3). The organic layer was washed with water (2 ml×3) and dried over anhydrous magnesium sulfate. The drying agent was filtered off, and the filtrate was concentrated under reduced pressure to give a pale yellow oily product. The product thus obtained was purified by silica gel column chromatography to give 170 mg of a white solid. The product was confirmed to be 3-[4-(1-cyanoethyl)-7-fluoro-2H-1,4-benzoxazine-3(4H)-one-6-yl]-5-isopropylidene-1,3-oxazolidine-2,4-dione (Compound 15) from the analytical data of $^1$H-NMR and IR spectra, etc.

EXAMPLE 16

(a)

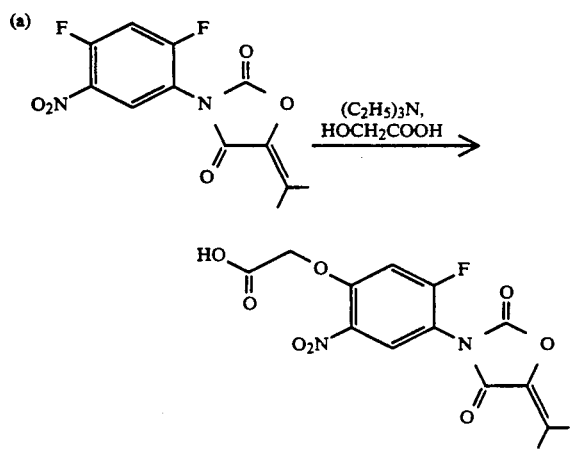

304 mg (1.02 mmol) of 3-(2,4-difluoro-5-nitrophenyl)-5-isopropylidene-1,3-oxazolidine-2,4-dione and 203 mg (2.67 mmol) of glycolic acid were charged into a 50 cc round-bottom flask and melted by heating in an oil bath at 100° C. Then, 0.5 ml of triethylamine was added dropwise thereto, and the mixture was stirred at 100° C. for 1 hour. After completion of the reaction, 1N hydrochloric acid (25 ml) and water (25 ml) were added to the reaction mixture, which was then extracted with ethyl acetate (25 ml×3). The organic layer was washed with water (25 ml×3) and dried over anhydrous magnesium sulfate. The drying agent was filtered off, and the solvent was distilled off from the filtrate under reduced pressure to give 168 mg of a yellow oily product. The resulting product was confirmed to be 3-(2-fluoro-4-hydroxycarbonylmethyloxy-5-nitro phenyl)isopropylidene-1,3-oxazolidine-2,4-dione from the analytical date of $^1$H-NMR and IR spectra, etc.

$^1$H-NMR (CDCl$_3$): δ2.08 (3H, s), 2.30 (3H, s), 4.88 (2H, s), 7.07 (1H, d, $J_{HF}$=10.0 Hz), 8.21 (1H, d, $J_{HF}$=7.0 Hz), 10.9 (1H, brs), ppm:

IR (neat): 1910, 1730, 1685 cm$^{-1}$.

(a')

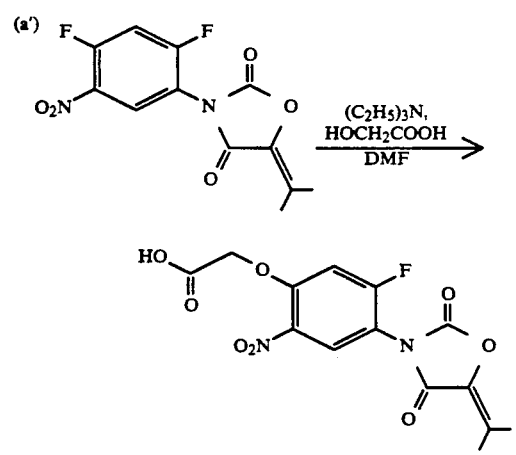

308 mg (1.03 mmol) of 3-(2,4-difluoro-5-nitrophenyl)-5-isopropylidene-1,3-oxazolidine-2,4-dione and 81 mg (1.01 mmol) of glycolic acid were charged into a 50 cc round-bottom flask and dissolved in 10 ml of N,N-dimethylformamide. Then, 0.3 ml of triethylamine was added dropwise thereto, and the mixture was stirred at 100° C. for 7 hours. After completion of the reaction, 1N hydrochloric acid (25 ml) and water (25 ml) were added to the reaction mixture which was then extracted with ethyl acetate (25 ml×4). The organic layer was washed with brine (25 ml) and dried over anhydrous magnesium sulfate. The drying agent was filtered off, and the solvent was distilled off from the filtrate under redused pressure to give 80 mg of a yellow oily product. The resulting product was confirmed to be 3-(2-fluoro-4-hydroxycarbonylmethyloxy-5-nitrophenyl)-5-isopropylidene-1,3-oxazolidine-2,4-dione from the analytical data of $^1$H-NMR and IR spectra, etc.

(b) (Compound 1)

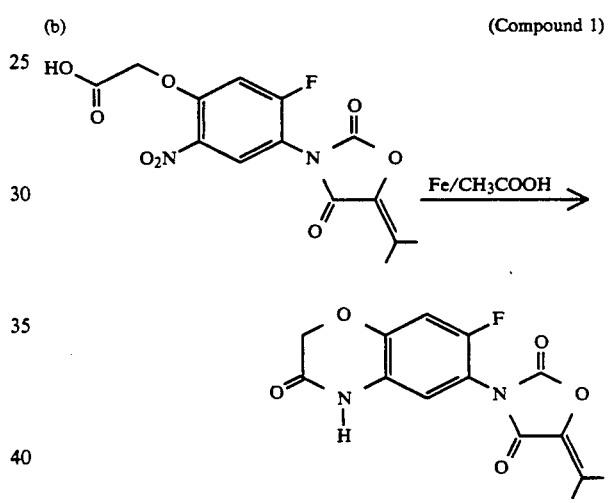

1.4 g of reduced iron was charged into a 3-necked flask equipped with a mechanical stirrer, a dropping funnel and a reflux condenser, and 10 ml of acetic acid was added thereto. The mixture was then heated under reflux until the mixture turned into a white suspension. A solution of 168 mg of 3-(2-fluoro-4-hydroxycabonyl-methyloxy-5-nitrophenyl)-5-iso-propylidene-1,3-oxazolidine-2,4-dione in 10 ml of acetic acid was added dropwise to the suspension. After completion of the addition, the mixture was stirred at 80° C. for 3 hours and, after cooling, insoluble materials in the reaction mixture were filtered off. 50 ml of water was added to the filtrate, and the mixture was extracted with ethyl acetate (20 ml×4). The organic layer was washed with water (20 ml) and dried over anhydrous magnesium sulfate. The drying agent was filtered off, and the solvent was removed under reduced pressure to give 80 mg of a pale brown solid. The product thus obtained was confirmed to be 3-(7-fluoro-2H-1,4-benzoxazine-3(4H)-one-6-yl)-5-isopropylidene-1,3-oxazolidine-2,4-dione (Compound 1) from the analytical data of $^1$H-NMR and IR spectra, etc.

EXAMPLE 17

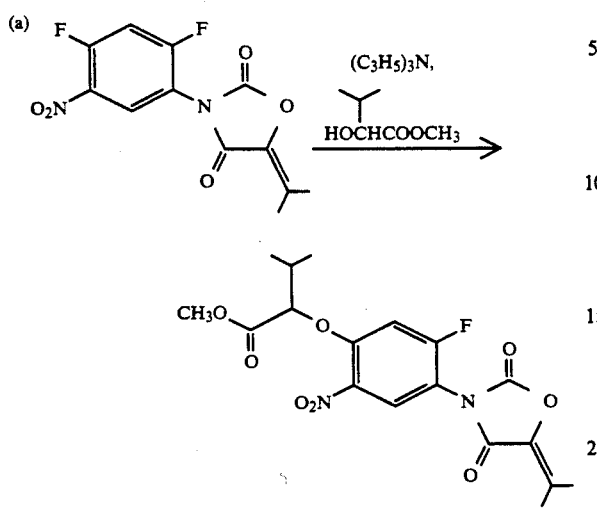

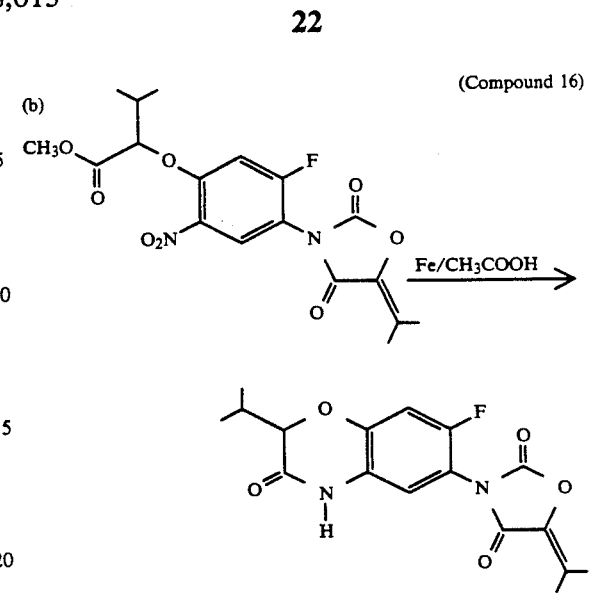

(Compound 16)

A mixture of 298 mg (1.0 mmol) of 3-(2,4-difluoro-5-nitrophenyl)-5-isopropylidene-1,3-oxazolidine-2,4-dione, 1.0 g (7.6 mmol) of methyl 2-hydroxyisovalerate and 0.3 ml of triethylamine was reacted overnight under a pressure of 2500 atm. at room temperature using a high-pressure reactor. After completion of the reaction, 50 ml of 0.1N hydrochloric acid was added thereto, and the mixture was extracted with ethyl acetate (25 ml×2). The organic layer was washed with water (20 ml×5) and dried over anhydrous magnesium sulfate. After the drying agent was filtered off, the solvent was distilled off under reduced pressure to give a pale yellow oily product. The product was isolated and purified by silica gel column chromatography to give 319 mg of a white solid. The product thus giveed was confirmed to be 3-[2-fluoro-4-(1-methoxycarbonyl)-isobutyloxy-5-nitrophenyl]-5-isopropylidene-1,3-oxazolidine-2,4-dione from the analytical data of $^1$H-NMR and IR spectra, etc.

$^1$H-NMR (CDCl$^3$): δ1.03 (6H, d, J=6.0 Hz), 1.98 (3H, s), 2.20 (3H, s), 2.30 (1H, m), 3.70 (3H, s), 4.47 (1H, d, J=5.0 Hz), 6.68 (1H, d, J$_{HF}$=11.0 Hz), 7.98 (1H, d, J$_{HF}$=8.0 Hz), ppm:

IR (neat): 2980, 1820, 1760, 1745 cm$^{-1}$.

1.2 g (20 mmol) of reduced iron was charged into a 3-necked flask equipped with a mechanical stirrer, a dropping funnel and a reflux condenser, and 10 ml of acetic acid was added thereto. The mixture was then heated under reflux until the mixture turned into a white suspension. A solution of 253 mg (0.62 mmol) of 3-[2-fluoro-4-(1-methoxycarbonyl)-isobutyloxy-5-nitrophenyl]-5-isopropylidene-1,3-oxazolidine-2,4-dione in 10 ml of acetic acid was added dropwise thereto under reflux. After completion of the addition, the mixture was stirred under reflux for 1 hour and, after cooling, insoluble materials in the reaction mixture were filtered off. 25 ml of 1N hydrochloric acid was added to the resulting solution and the mixture was extracted with ethyl acetate (25 ml×3). The organic layer was washed with water (10 ml×3) and dried over anhydrous magnesium sulfate. The drying agent was filtered off, and the solvent was removed under reduced pressure to give a brown solid. The resulting solid was recrystalized from hexane to give a pale brown solid product. The product thus obtained was confirmed to be 3-(7-fluoro-2-isopropyl-2H-1,4-benzoxazine-3(4H)-one-6-yl)-5-isopropylidene-1,3-oxazolidine-2,4-dione (Compound 16).

The physical properties and the elemental analysis of the benzoxazinone compounds prepared in the above Examples 1 to 17 are shown in Table 2 below, and the values of $^1$H-NMR and IR spectra of these compounds are shown in Table 3 below.

TABLE 2

| Compound No. | Melting point (°C.) | Empirical formula | C (%) Found | C (%) Calc'd | H (%) Found | H (%) Calc'd | N (%) Found | N (%) Calc'd | Optical Rotation [α]$_D$ (20° C., acetone) |
|---|---|---|---|---|---|---|---|---|---|
| 1 | 222–223 | C$_{14}$H$_{11}$FN$_2$O$_5$ | 54.91 | 54.55 | 3.62 | 3.81 | 9.15 | 8.80 | |
| 2 | 219–220 | C$_{15}$H$_{13}$FN$_2$O$_5$ | 56.02 | 56.25 | 4.07 | 4.09 | 8.37 | 8.75 | 8.21 (C = 1.12) |
| 3 | 200–201 | C$_{15}$H$_{13}$FN$_2$O$_5$ | 56.25 | 56.05 | 4.09 | 4.04 | 8.75 | 8.61 | |
| 4 | 120–121 | C$_{20}$H$_{23}$FN$_2$O$_5$ | 61.53 | 61.63 | 5.94 | 5.92 | 7.18 | 7.15 | |
| 5 | 166–168 | C$_{17}$H$_{15}$FN$_2$O$_5$ | 58.59 | 58.96 | 4.46 | 4.37 | 7.80 | 8.09 | |
| 6 | 214–215 | C$_{21}$H$_{17}$FN$_2$O$_5$ | 63.38 | 63.64 | 4.36 | 4.32 | 7.06 | 7.07 | |
| 7 | 189–191 | C$_{18}$H$_{17}$FN$_2$O$_5$ | 59.79 | 60.00 | 4.67 | 4.76 | 7.81 | 7.77 | |
| 8 | 194–195 | C$_{17}$H$_{13}$FN$_2$O$_5$ | 59.31 | 58.92 | 3.81 | 3.99 | 8.14 | 7.78 | |
| 9 | 177–198 | C$_{16}$H$_{15}$FN$_2$O$_5$ | 57.18 | 57.49 | 4.86 | 4.52 | 7.95 | 8.38 | 20.19 (C = 1.00) |
| 10 | oil | C$_{21}$H$_{25}$FN$_2$O$_5$ | 61.95 | 62.37 | 6.59 | 6.23 | 6.58 | 6.93 | 11.72 (C = 1.62) |
| 11 | 138–139 | C$_{18}$H$_{17}$FN$_2$O$_5$ | 59.84 | 60.00 | 4.70 | 4.76 | 7.68 | 7.77 | 22.00 (C = 1.30) |
| 12 | 186–190 | C$_{18}$H$_{15}$FN$_2$O$_5$ | 60.22 | 60.34 | 4.15 | 4.22 | 7.54 | 7.82 | 17.00 (C = 0.80) |
| 13 | 150–152 | C$_{17}$H$_{17}$FN$_2$O$_5$ | 58.62 | 58.64 | 5.27 | 4.92 | 7.93 | 8.04 | |
| 14 | 87–91 | C$_{16}$H$_{12}$FN$_3$O$_5$ | 55.40 | 55.66 | 3.61 | 3.50 | 11.91 | 12.17 | |
| 15 | 85–89 | C$_{17}$H$_{14}$FN$_3$O$_5$ | 56.72 | 56.83 | 4.10 | 3.93 | 11.41 | 11.69 | |

TABLE 2-continued

| Compound No. | Melting point (°C.) | Empirical formula | C (%) Found | C (%) Calc'd | H (%) Found | H (%) Calc'd | N (%) Found | N (%) Calc'd | Optical Rotation $[\alpha]_D$ (20° C., acetone) |
|---|---|---|---|---|---|---|---|---|---|
| 16 | 95-100 | $C_{17}H_{15}FN_2O_5$ | 58.96 | 58.96 | 4.39 | 4.37 | 7.65 | 8.09 | |

TABLE 3

| Compound No. | $^1$H-NMR Spectrum(CDCl$_3$, TMS, δ ppm) | IR Spectrum (cm$^{-1}$) |
|---|---|---|
| 1 | 2.03(3H, s), 2.26(3H, s), 4.56(2H, s), 6.81(1H, d, $J_{HF}$=10.5Hz) 6.90(1H, d, $J_{HF}$=6.0Hz), 7.43(1H, br). (DCDl$_3$+d$_6$-DMSO) | 1815, 1745, 1695 |
| 2 | 1.59(3H, d, J=6.3Hz), 2.04(3H, s), 2.27(3H, s), 4.68(1H, q, J=6.3Hz), 6.78(1H, d, $J_{HF}$=6.3Hz), 6.85(1H, d, $J_{HF}$=10.5Hz), 9.20(1H, br) | 1815, 1745, 1690 |
| 3 | 2.05(3H, s), 2.28(3H, s), 3.32(3H, s), 4.65(2H, s), 6.86(1H, d, $J_{HF}$=6.9Hz), 6.89(1H, d, $J_{HF}$=10.5Hz) | 1825, 1730, 1690 |
| 4 | 1.43(3H, br), 1.82(9H, br), 2.04(3H, s), 2.27(3H, s), 3.89(2H, brt), 4.60(2H, s), 6.82(1H, d, $J_{HF}$=6.6Hz), 6.86(1H, d, $J_{HF}$=9.6Hz) | 1810, 1745, 1695 |
| 5 | 2.04(3H, s), 2.27(3H, s), 4.51(2H, ddd, J=1.5, 1.5, 5.1Hz), 5.19(1H, ddt, J=1.4, 16.2, 1.5Hz), 5.23(1H, ddt, J=1.4, 7.8, 1.5Hz), 5.82(1H, ddt, J=16.2, 7.8, 5.7Hz), 6.85(1H, d, $J_{HF}$=6.9Hz), 6.88(1H, d, $J_{HF}$=10.2Hz) | 1810, 1740, 1690 |
| 6 | 2.01(3H, s), 2.24(1H, t, J=2.1Hz), 4.74(2H, s), 5.10(2H, s), 6.78(1H, d, $J_{HF}$=7.2Hz), 7.23(1H, d, $J_{HF}$=10.5Hz), 7.23(5H, s) | 1810, 1745, 1690 |
| 7 | 1.70(3H, dd, J=6.5, 1.5Hz), 2.06(3H, s), 2.30(3H, s), 4.46(2H, dd, J=5.6, 1.4Hz), 4.67(2H, s), 5.45(1H, dtq, J=15.4, 5.6, 1.5Hz), 5.70(1H, dqt, J=15.4, 6.5, 1.4Hz), 6.90(1H, d, $J_{HF}$=9.8Hz), 6.92(1H, d, $J_{HF}$=6.8Hz), | 1810, 1740, 1690 |
| 8 | 2.03(3H, s), 2.23(1H, t, J=2.1Hz), 2.27(3H, s), 4.63(2H, d, J=2.1Hz), 4.65(2H, s), 6.90(1H, d, $J_{HF}$=9.6Hz), 7.09(1H, d, $J_{HF}$=6.3Hz) | 1810, 1740, 1690 |
| 9 | 1.57(3H, d, J=6.3Hz), 2.04(3H, s), 2.27(3H, s), 3.30(3H, s), 4.67(1H, q, J=6.3Hz), 6.82(1H, d, $J_{HF}$=6.6Hz), 6.87(1H, d, $J_{HF}$=10.5Hz) | 1810, 1745, 1690 |
| 10 | 0.87(3H, brt), 1.32(8H, br), 1.58(3H, d, J=6.6Hz), 2.04(3H, s), 2.28(3H, s), 4.64(1H, q, J=6.6Hz), 6.84(1H, d, $J_{HF}$=6.6Hz), 6.87(1H, d, $J_{HF}$=10.2Hz) | 1820, 1745, 1690 |
| 11 | 1.59(3H, d, J=6.9Hz), 2.04(3H, s), 2.28(3H, s), 4.48(2H, ddd, J=5.4, 1.5, 1.4Hz), 4.69(1H, q, J=6.9Hz), 5.10(1H, ddt, J=17.3, 1.2, 1.5Hz), 5.22(1H, ddt, J=9.3, 1.2, 1.4Hz), 5.83(1H, ddt, J=17.3, 9.3, 5.4Hz), 6.83(1H, d, $J_{HF}$=6.0Hz), 6.88(1H, d, $J_{HF}$=9.9Hz) | 1815, 1740, 1690 |
| 12 | 1.57(3H, d, J=6.6Hz), 2.03(3H, s), 2.25(1H, t, J=1.5Hz), 2.27(3H, s), 4.63(2H, d, J=1.5Hz), 4.68(1H, d, J=6.6Hz), 6.89(1H, d, $J_{HF}$=9.9Hz), 7.05(1H, d, $J_{HF}$=6.5Hz) | 1810, 1745, 1695 |
| 13 | 1.50(6H, d, J=6.6Hz), 2.03(3H, s), 2.27(3H, s), 4.50(2H, s), 4.65(1H, sep, J=6.6Hz), 6.89(1H, d, $J_{HF}$=10.2Hz), 7.02(1H, d, $J_{HF}$=7.2Hz). | 1810, 1745, 1685 |
| 14 | 2.07(3H, s), 2.30(3H, s), 4.75(2H, s), 4.82(2H, s), 7.01(1H, d, $J_{HF}$=9.9Hz), 7.03(1H, d, $J_{HF}$=6.3Hz) | 1810, 1740, 1705 |
| 15 | 1.70(3H, d, J=7.2Hz), 2.03(3H, s), 2.26(3H, s), 4.64(2H, d, J=2.1Hz), 6.01(1H, q, J=7.2Hz), 6.98(1H, d, $J_{HF}$=10.2Hz), 7.30(1H, d, $J_{HF}$=6.0Hz) | 1810, 1740, 1695 |
| 16 | 0.92(3H, d, J=7.0Hz), 1.00(3H, d, J=7.0Hz), 2.03(3H, s), 2.15(1H, m), 2.23(3H, s), 4.30(1H, d, J=6.0Hz), 6.70(1H, d, $J_{HF}$=6.0Hz), 6.80(1H, d, $J_{HF}$=10.0Hz), 9.45(1H, brs) | 1820, 1730, 1690 |

The benzoxazinone compounds according to the present invention represented by the formula (I) above have an excellent herbicidal activity as described above.

In using the benzoxazinone compounds of this invention as herbicidal agents, the compounds per se can be used, but generally they are preferably used in the form of a herbicidal composition in admixture with one or more conventional auxiliary agents which are agriculturally acceptable. Examples of the auxiliary agent which can be used includes various carriers, vulcanizing agent, solvents, surface active agents, stabilizers and the like. The compounds of the present invention are preferably used by blending with these auxiliary agent in a conventional form of herbicidal compositions such as wettable powders, emulsions, powders or dust, granules, etc.

Examples of the solvent which can be suitably used as an auxiliary agent in the herbicidal composition of this invention include, for example, water, alcohols, ketones, ethers, aliphatic and aromatic hydrocarbons, halogenated hydrocarbons, acid amides, esters, nitriles, or a mixture of these solvents.

Examples of the vulcanizing agents which can be used in the herbicidal composition include mineral powders, for example, clays such as kaolin or bentonite, talcs such as talc or pyrophyllite, oxides such as diatomaceous earth or white carbon, and vegetable powders such as soybean powder, carboxymethyl cellulose, etc.

Also, surface active agents can be used in the herbicidal composition of this invention as a spreading agent, a dispersing agent, an emulsifying agent or a penetrating agent. Examples of the surface active agents include non-ionic surface active agents, cationic surface active agents and amphoteric surface active agents. These surface active agents can be used alone or as a mixture of two or more agents depending upon the purpose of use.

A herbicidal composition containing the benzoxazinone compound of the present invention can be used for soil treatment, water surface treatment, the stalk and leaves treatment, and the like, and exhibits a particularly excellent herbicidal activity when it is applied during the period before or just after germination of the weeds to be killed.

Further, the herbicidal composition of this invention can also contain other active agents which do not adversely affect the herbicidal activity of the benzoxazinone compounds of this invention, for example, herbicides, insecticides, fungicides, plant growth regulators and the like, or can be used in combination with these active agents.

Examples of herbicidal compositions containing the benzoxazinone compound of this invention as an active component, and the herbicidal effects of these compositions are shown in detail in the following examples. Unless otherwise indicated, all parts are by weight.

EXAMPLE 18

Preparation of Emulsion 20 parts of Compound 1 of the present invention, 35 parts of xylene, 40 parts of cyclohexanone and 5 parts of Solbol 900A (a trademark for the product of Toho chemical Co., Ltd.) were blended uniformly to form an emulsion.

An emulsion was also prepared in the same manner as described above but using one of the other compounds of the present invention instead of Compound 1 used above.

EXAMPLE 19

Preparation of Wettable Powder

A mixture of 50 parts of Compound 1 of the present invention, 25 parts of diatomaceous earth, 22 parts of clay and 3 parts of Lunox R 100C (a trademark for the product of Toho Chemical Co., Ltd.) was blended and milled uniformly, and a predetermined amount of water was added to the resulting mixture to form a wettable powder.

A wettable powder was also prepared in the same manner as described above but using one of the other compounds of the present invention instead of Compound 1 used above.

EXAMPLE 20

Preparation of Granules

A mixture of 5 parts of compound 1 of the present invention, 35 parts of bentonite, 55 parts of talc and 5 parts of sodium ligninsulfonate was blended and milled uniformly and water was, then; added thereto. The resulting mixture was thoroughly kneaded, extruded from a granulator, and the resulting granules were dried and subjected to a treatment for regulating the grain size to form desired granules.

A granule preparation was also prepared in the same manner as described above but using any of other compounds of the present invention instead of Compound 1 used above.

EXAMPLE 21

Herbicidal Effect on Weeds in Paddy Field

Paddy field soil was placed in Wagnel pots of 1/5000 Are, and seeds of *Echinochloa crus-galli, Monochoria vaginalis* and *Ammania multiflora* were sown, and seedings of rice plant ("Nihonbare" species) of a 2-3 leaf time were also transplanted in the pots. The pots were kept under wet conditions. After 5 days, the surface of the pots was submerged to a water depth of 4 cm, and the water surface was treated with predetermined amounts of the diluted wettable powder prepare in Example 19 or the diluted emulsion prepared in Example 18 in amounts of 20 g, 10 g, or 5 g of the benzoxazinone compound.

On the 20th day after this treatment, the herbicidal effect on the test weeds and the phytotoxicity to the rice plant were evaluated according to the following rating. The results are shown in Table 4 below.

| | Evaluation Rating | |
|---|---|---|
| Herbicidal Activity | Proportion of Weeds (%) | Phytotoxicity |
| 0 | 81 to 100 | −: No damage |
| 1 | 61 to 80 | +: Slight damage |
| 2 | 41 to 60 | ++: Small damage |
| 3 | 21 to 40 | +++: Medium damage |
| 4 | 6 to 20 | ++++: Heavy damage |
| 5 | 0 to 5 | X: Dead |

TABLE 4

Herbicidal Effect on Weeds in Paddy Field

| Test Compound | Amount Applied (g/Are) | Degree of Herbicidal Effect | | | Phytotoxicity to Rice Plant |
|---|---|---|---|---|---|
| | | E. Crus-galli | M vaginalis | A. multiflora | |
| 1 | 20 | 5 | 5 | 5 | |
| | 10 | 4 | 5 | 5 | + |
| | 5 | 3 | 5 | 5 | − |
| 2 | 20 | 4 | 5 | 5 | |
| | 10 | 3 | 5 | 5 | + |
| | 5 | 3 | 5 | 5 | − |
| 3 | 20 | 5 | 5 | 5 | |
| | 10 | 4 | 5 | 5 | |
| | 5 | 3 | 5 | 5 | + |
| 4 | 20 | 4 | 5 | 5 | + |
| | 10 | 3 | 5 | 5 | − |
| | 5 | 2 | 5 | 5 | − |
| 5 | 20 | 5 | 5 | 5 | |
| | 10 | 5 | 5 | 5 | |
| | 5 | 5 | 5 | 5 | − |
| 6 | 20 | 2 | 5 | 5 | |
| | 10 | 1 | 4 | 4 | − |
| | 5 | 0 | 3 | 4 | − |
| 7 | 20 | 5 | 5 | 5 | + |
| | 10 | 5 | 5 | 5 | + |
| | 5 | 5 | 5 | 5 | − |
| 8 | 20 | 5 | 5 | 5 | |
| | 10 | 5 | 5 | 5 | |
| | 5 | 5 | 5 | 5 | + |
| 9 | 20 | 5 | 5 | 5 | |
| | 10 | 5 | 5 | 5 | + |
| | 5 | 4 | 5 | 5 | + |
| 10 | 20 | 5 | 5 | 5 | + |
| | 10 | 5 | 5 | 5 | − |
| | 5 | 5 | 5 | 5 | − |
| 11 | 20 | 5 | 5 | 5 | |
| | 10 | 5 | 5 | 5 | |
| | 5 | 5 | 5 | 5 | − |
| 12 | 20 | 5 | 5 | 5 | |
| | 10 | 5 | 5 | 5 | |
| | 5 | 5 | 5 | 5 | + |
| 13 | 20 | 5 | 5 | 5 | + |
| | 10 | 5 | 5 | 5 | + |
| | 5 | 5 | 5 | 5 | − |
| 14 | 20 | 5 | 5 | 5 | + |
| | 10 | 5 | 5 | 5 | + |
| | 5 | 5 | 5 | 5 | − |
| 15 | 20 | 5 | 5 | 5 | + |
| | 10 | 5 | 5 | 5 | − |
| | 5 | 5 | 5 | 5 | − |
| 16 | 20 | 3 | 5 | 5 | − |
| | 10 | 2 | 5 | 4 | − |
| | 5 | 1 | 4 | 4 | − |
| Control (MO) | 20 | 5 | 5 | 5 | + |
| | 10 | 4 | 4 | 5 | − |

TABLE 4-continued

| | | Herbicidal Effect on Weeds in Paddy Field | | | |
|---|---|---|---|---|---|
| Test Compound | Amount Applied (g/Are) | Degree of Herbicidal Effect | | | Phyto-toxicity to Rice Plant |
| | | E. Crus-galli | M. vaginalis | A. multiflora | |
| | 5 | 3 | 4 | 4 | — |

EXAMPLE 22

Herbicidal Effect of Soil Treatment on Field Weeds.

Field soil was placed in vats having an area of 16 × 11 cm² and a depth of 7 cm, and seeds of *Digitaria adscendens*, *Chenopodium album*, *Amaranthus lividus* and Soybean were sown and then covered with the soil to a depth of 1 cm. Next day, predetermined amounts of a diluted solution of the wettable powder prepared in Example 19 or a diluted solution of the emulsion prepared in Example 19 or a diluted solution of the emulsion prepared in Example 18 were applied uniformly on the soil at an amount of 20 g, 10 g or 5 g of the benzoxazinone compound.

On the 20th day after the treatment, the herbicidal effect on the test weeds and phytotoxicity to the soybean were evaluated in the same manner as in Example 21. The results are shown in Table 5 below.

TABLE 5

| | | Herbicidal Effect on Field Weeds by Stem-Leaf Treatment | | | |
|---|---|---|---|---|---|
| Test Compound | Amount Applied (ppm) | Degree of Herbicidal Effect | | | Phyto-toxicity to Soybean |
| | | D. adscendens | C. album | A. lividus | |
| 1 | 20 | 4 | 5 | 5 | — |
| | 10 | 3 | 5 | 5 | — |
| | 5 | 2 | 3 | 4 | — |
| 2 | 20 | 3 | 4 | 4 | — |
| | 10 | 2 | 3 | 3 | — |
| | 5 | 1 | 2 | 3 | — |
| 3 | 20 | 5 | 5 | 5 | — |
| | 10 | 5 | 5 | 5 | — |
| | 5 | 4 | 4 | 4 | — |
| 4 | 20 | 2 | 4 | 4 | + |
| | 10 | 1 | 3 | 4 | — |
| | 5 | 0 | 2 | 3 | — |
| 5 | 20 | 5 | 5 | 5 | + |
| | 10 | 5 | 5 | 5 | — |
| | 5 | 5 | 5 | 5 | — |
| 6 | 20 | 0 | 1 | 1 | — |
| | 10 | | | | |
| | 5 | | | | |
| 7 | 20 | 5 | 5 | 5 | — |
| | 10 | 5 | 4 | 5 | — |
| | 5 | 4 | 3 | 4 | — |
| 8 | 20 | 5 | 5 | 5 | |
| | 10 | 5 | 5 | 5 | + |
| | 5 | 5 | 5 | 5 | — |
| 9 | 20 | 5 | 5 | 5 | — |
| | 10 | 4 | 5 | 5 | — |
| | 5 | 3 | 4 | 5 | — |
| 10 | 20 | 3 | 4 | 4 | — |
| | 10 | 3 | 3 | 4 | — |
| | 5 | 2 | 2 | 3 | — |
| 11 | 20 | 5 | 5 | 5 | + |
| | 10 | 5 | 5 | 5 | — |
| | 5 | 4 | 5 | 5 | — |
| 12 | 20 | 5 | 5 | 5 | + |
| | 10 | 5 | 5 | 5 | + |
| | 5 | 4 | 5 | 5 | — |
| 13 | 20 | 5 | 5 | 5 | + |
| | 10 | 5 | 5 | 5 | — |
| | 5 | 5 | 5 | 5 | — |
| 14 | 20 | 5 | 5 | 5 | — |
| | 10 | 4 | 5 | 5 | — |
| | 5 | 3 | 4 | 4 | — |

TABLE 5-continued

| | | Herbicidal Effect on Field Weeds by Stem-Leaf Treatment | | | |
|---|---|---|---|---|---|
| Test Compound | Amount Applied (ppm) | Degree of Herbicidal Effect | | | Phyto-toxicity to Soybean |
| | | D. adscendens | C. album | A. lividus | |
| 15 | 20 | 5 | 5 | 5 | — |
| | 10 | 4 | 4 | 5 | — |
| | 5 | 3 | 4 | 4 | — |
| 16 | 20 | 2 | 3 | 3 | — |
| | 10 | 1 | 2 | 2 | — |
| | 5 | 0 | 1 | 2 | — |
| Control (MO) | 20 | 5 | 5 | 4 | + |
| | 10 | 4 | 4 | 3 | — |
| | 5 | 2 | 3 | 2 | — |

EXAMPLE 23

Herbicidal Effect on Field Weeds by Stalk and Leaves Treatment

Field soil was placed in vats having an area of 16 × 11 cm² and a depth of 7 cm, and seeds of *Polygonum logisetum*, *Chenopodium album*, *Amaranthus lividus* and corn were sown. After 15 days, predetermined amounts of a diluted solution of the wettable powder prepared in Example 19 or a diluted solution of the emulsion prepared in Example 18 were sprayed on the stalk and leaves of the grown plants in an amount of 10 liters per Are. On the 20th day after the treatment, the herbicidal effect on the test weeds and phytotoxicity to the corn plant were evaluated in the same manner as described in Example 21. The results are shown in Table 6 below.

TABLE 6

| | | Herbicidal Effect on Field Weeds by Stalk and Leaves Treatment | | | |
|---|---|---|---|---|---|
| Test Compound | Amount Applied (ppm) | Degree of Herbicidal Effect | | | Phyto-toxicity to Corn |
| | | C. album | A. lividus | P. logesetum | |
| 1 | 2000 | 5 | 5 | 5 | + |
| | 1000 | 4 | 5 | 5 | — |
| | 500 | 3 | 4 | 4 | — |
| 2 | 2000 | 3 | 4 | 4 | |
| | 1000 | 2 | 3 | 3 | + |
| | 500 | 1 | 2 | 2 | — |
| 3 | 2000 | 5 | 5 | 5 | |
| | 1000 | 4 | 4 | 4 | + |
| | 500 | 1 | 3 | 3 | — |
| 4 | 2000 | 5 | 5 | 5 | + |
| | 1000 | 2 | 4 | 4 | — |
| | 500 | 1 | 3 | 3 | — |
| 5 | 2000 | 5 | 5 | 5 | |
| | 1000 | 5 | 5 | 5 | + |
| | 500 | 3 | 4 | 5 | — |
| 6 | 2000 | 3 | 3 | 3 | + |
| | 1000 | 2 | 2 | 2 | — |
| | 500 | 1 | 1 | 1 | — |
| 7 | 2000 | 5 | 5 | 5 | + |
| | 1000 | 5 | 5 | 5 | + |
| | 500 | 3 | 4 | 4 | — |
| 8 | 2000 | 5 | 5 | 5 | |
| | 1000 | 5 | 5 | 5 | |
| | 500 | 5 | 5 | 5 | + |
| 9 | 2000 | 5 | 5 | 5 | |
| | 1000 | 4 | 5 | 5 | + |
| | 500 | 3 | 4 | 4 | — |
| 10 | 2000 | 5 | 5 | 5 | |
| | 1000 | 4 | 5 | 4 | + |
| | 500 | 2 | 4 | 2 | — |
| 11 | 2000 | 5 | 5 | 5 | |
| | 1000 | 4 | 4 | 5 | + |
| | 500 | 3 | 3 | 4 | — |
| 12 | 2000 | 5 | 5 | 5 | |
| | 1000 | 5 | 5 | 5 | |
| | 500 | 2 | 3 | 5 | + |
| 13 | 2000 | 5 | 5 | 5 | + |
| | 1000 | 5 | 5 | 5 | + |

TABLE 6-continued

| | | Degree of Herbicidal Effect | | | |
|---|---|---|---|---|---|
| Test Compound | Amount Applied (ppm) | C. album | A. lividus | P. logesetum | Phytotoxicity to Corn |
| 14 | 500 | 4 | 5 | 5 | — |
| | 2000 | 5 | 5 | 5 | |
| | 1000 | 4 | 5 | 4 | + |
| | 500 | 3 | 4 | 3 | — |
| 15 | 2000 | 5 | 5 | 5 | + |
| | 1000 | 4 | 5 | 4 | + |
| | 500 | 4 | 4 | 4 | — |
| 16 | 2000 | 4 | 4 | 4 | + |
| | 1000 | 2 | 3 | 3 | — |
| | 500 | 1 | 2 | 2 | — |
| (Control) | 2000 | 5 | 5 | 5 | ++ |
| (MO) | 1000 | 4 | 4 | 4 | + |
| | 500 | 4 | 3 | 3 | — |

What is claimed is:

1. A benzoxazinone compound represented by the formula (I):

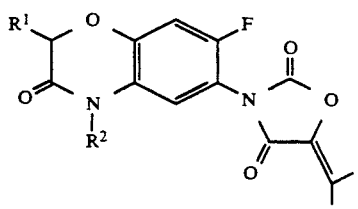

wherein $R^1$ represents a hydrogen atom or an alkyl group, and $R^2$ represents a hydrogen atom, an alkyl group, a cyanoalkyl group, an alkenyl group, an alkynyl group or an aralkyl group.

2. A benzoxazinone compound as claimed in claim 1, wherein $R^1$ represents an alkyl group having 1 to 4 carbon atoms.

3. A benzoxazinone compound as claimed in claim 1, wherein $R^2$ represents an alkyl group having 1 to 8 carbon atoms.

4. A benzoxazinone compound as claimed in claim 1, wherein $R^2$ represents a cyanoalkyl group having 1 to 4 carbon atoms in the alkyl moiety thereof. carbon atoms in the alkyl moiety thereof.

5. A benzoxazinone compound as claimed in claim 1, wherein $R^2$ represents an alkenyl group having 3 to 6 carbon atoms.

6. A benzoxazinone compound as claimed in claim 1, wherein $R^2$ represents an alkynyl group having 3 to 6 carbon atoms.

7. A benzoxazinone compound as claimed in claim 1, wherein $R^2$ represents an aralkyl group having 7 to 10 carbon atoms.

8. A herbicidal composition which comprises an agriculturally acceptable carrier or diluent and at least one of benzoxazinone compounds represented by the formula (I):

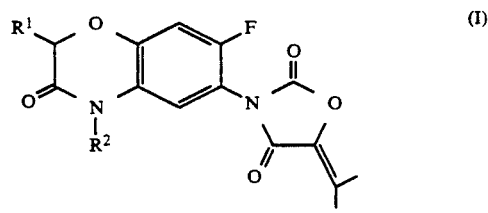

wherein $R^1$ represents a hydrogen atom or an alkyl group, and $R^2$ represents a hydrogen atm, an alkyl group, a cyanoalkyl group, an alkenyl group, an alkynyl group or an aralkyl group.

9. A herbicidal composition as claimed in claim 8, wherein said composition is in the form of a wettable powder, an emulsion, a dust preparation or a granule preparation.

* * * * *